United States Patent [19]

Poussou

[11] Patent Number: 4,906,425
[45] Date of Patent: Mar. 6, 1990

[54] METHODS TO OBTAIN CORRECTED IMPRESSIONS OF FEET SO AS TO PRODUCE CORRECTIVE SOLES

[76] Inventor: Alain A. Poussou, Les Myosotis - Bâtiment A - 190, Avenue des Caillols, 13012 - Marseille, France

[21] Appl. No.: 233,664

[22] Filed: Aug. 18, 1988

[30] Foreign Application Priority Data

Oct. 2, 1987 [FR] France ................ 87 13618

[51] Int. Cl.⁴ ............... B29C 33/42; B29C 33/54
[52] U.S. Cl. ........................... 264/102; 264/220; 264/222; 264/223; 264/227; 264/DIG. 30; 264/DIG. 78; 425/2
[58] Field of Search ........... 264/101, 102, 220, 222, 264/223, 225, 227, 313, 517, 571, DIG. 30, DIG. 78; 425/2

[56] References Cited

U.S. PATENT DOCUMENTS 2,177,304 10/1939 Murray ................... 264/313
2,424,278 7/1947 Kunkel ................... 264/222
2,472,754 6/1949 Mead ................... 264/DIG. 30
3,309,447 3/1967 Wegely ................... 264/223

FOREIGN PATENT DOCUMENTS

1234355 2/1967 Fed. Rep. of Germany .
2440540 11/1978 France .
2592282 12/1985 France .

Primary Examiner—Jeffery Thurlow
Assistant Examiner—Mathieu Vargot
Attorney, Agent, or Firm—Ladas & Parry

[57] ABSTRACT

A method to obtain corrected impressions of the foot so as to produce corrective soles including two or three superimposed rigid frames connected to a supporting structure secured by arms of different length joined to the supporting structure. Each frame is equipped with two flexible walls which, along with the frame, delimit a sealed enclosure filled with a granular material, the enclosure communicating with a suction device.

3 Claims, 5 Drawing Sheets

METHODS TO OBTAIN CORRECTED IMPRESSIONS OF FEET SO AS TO PRODUCE CORRECTIVE SOLES

FIELD OF THE INVENTION

BACKGROUND OF THE INVENTION

The present invention relates to the methods and devices designed to obtain the corrected impressions of feet so as to produce corrective soles or plantar ortheses or shoes comprising a corrective sole.

The technical sector of the invention is the one relating to the production of orthopedic shoes and soles.

OBJECT AND SUMMARY OF THE INVENTION

The methods are known which render it possible to obtain a negative or additional impression of the sole of the feet with the aid of a sealed ductile enclosure, for example a ductile pocket, which is filled with granular materials and is placed in a vacuum after a foot has been placed on the ductile wall which constitutes the upper face of the enclosure.

The U.S. Pat. No. A. 2,472,754 (W.J. MEAD) describes a method wherein a foot is placed when it is desired to obtain a mould inside a rigid container comprising a bottom and lateral walls and containing several sealed flexible pockets which are filled with a granular material mixed with a fluid. One of the pockets is placed on the on the bottom of the container under the sole of the foot laid flat. The other pockets are placed around and above the foot. These pockets are connected to a device for sucking up the fluid.

After the foot has been removed, the pockets e are put back into their position and a mould of the foot is made inside the cavity. This mould is used as a model to produce a shoelike shape reproducing the shape of the foot. It is also possible to obtain a model of the cavity by inserting in the latter a flexible pocket which inflates and is filled by a mixture of a granular material and a fluid and which solidifies by placing the pocket in a vacuum.

The device described may be used by shoe salesmen/women when selecting shoes adapted to the feet of a customer.

The French publication A. 2,162,020 (L. HAGGLUND) describes methods used to produce moulds having a form which corresponds to one part of the body of a patient.

According to these methods, a sealed flexible mould is used comprising at least one flexible wall applied against one part of the body, the said mould containing a granular material and means to place it in a vacuum. The method is provided to be able to produce orthopedic shoes, soles and plantar arch supports, without providing any detailed description of the method used in this case.

The German Pat. No. C. 1,170,114 (B. HULLMANN) describes a method and devices to obtain an impression of a foot laid flat wherein the foot is supported on a flexible membrane, which constitutes the upper Wall of a vessel filled with balls which is then placed in a vacuum via suction through a permeable wall.

The German Pat. No. C. 1,234,355 (B. HULLMANN) describes devices of the same type as the previous ones which, in addition, comprise a cover consisting of a frame bearing a ductile membrane which is applied by the vacuum against a modelable material placed between the two ductile walls in order to obtain an orthopedic element which reproduces the shape of the sole of the foot.

All these previous patents describe methods which make it possible to obtain a negative impression of the sole or the entire foot with the aid of an enclosure filled with a granular material and comprising at least one upper flexible wall on which the sole of the foot rests before the enclosure is placed in a vacuum.

Once a negative impression has been obtained, constituted by the upper flexible face of an enclosure filled with a granular material and kept in a vacuum, it is possible to make recessed corrections of this impression by locally pressing on the flexible wall in order to force back the granular material. On the other hand, it is difficult to make relief corrections of this negative impression or obtain an impression of the sole of the foot placed in a position different from the flat position in order to produce soles or elements of corrective soles. Moreover, if the recessed corrections are carried out on an enclosure which is separated from the vacuum placed device, bubbles or folds may form.

The aim of this invention is to procure means which enable both the relief and recessed negative impressions to be corrected by avoiding the formation of bubbles or folds which also enable negative and positive impressions to be obtained which reproduce the shape of the sole of the foot placed in a specific position so that it is then possible, on the basis of these corrected positive and negative impressions, to produce corrective soles or corrective sole elements with defects.

According to the invention, one method to obtain a negative impression of a foot is of the type wherein the foot rests on the upper flexible wall of a first sealed enclosure which is filled with granular materials, which includes a flexible lower wall and flexible upper wall and which is connected to a suction device enabling it to be placed in a vacuum in order to stiffen the said granular materials and retain a negative impression of the foot.

The objectives of the invention are obtained by a method wherein the said negative impression is corrected when the said enclosure is connected to the said suction device which sucks up inside the said enclosure.

Moreover, it is possible to obtain an additional positive impression of the corrected negative impression by placing on the latter a second sealed enclosure which is filled with granular materials, which includes a flexible upper wall and a flexible lower wall and which is connected to a suction device enabling it to be placed in a vacuum and by placing the said foot on the said upper wall and a corrective sole or corrective sole element is produced by using the said positive impression solely or in combination with the said corrected negative impression.

Another advantage of the invention is to locally correct the said recessed positive impression by raising up the said second enclosure and locally pressing on the lower wall of the latter whilst the enclosure is connected to the said suction device, the said second enclosure is again placed on the first enclosure and the said negative impression is corrected by pressing the said corrected positive impression against the upper face of the said first enclosure whilst the latter is connected to the said suction device and a corrective sole or corrective sole element is produced by using the said corrected positive impression solely or in combination with the said corrected negative impression.

Another advantage of the invention is to obtain a first corrected negative impression by placing corrective elements under the lower wall of a lower enclosure and then by pressing the foot on the upper wall of the said lower enclosure.

According to one preferred mode of embodiment, a corrected negative impression is obtained via the following operations:

a first negative impression is taken of the sole of the foot by pressing the latter onto the upper flexible wall of a lower enclosure filled with a granular material which is then placed in a vacuum;

the said first impression is subsequently corrected;

a second enclosure is paced, comprising a flexible upper wall and a flexible lower wall, on the said negative impression, the foot is pressed again on the upper wall of the said second enclosure and then the latter is placed in a vacuum so that the said upper wall of the second enclosure retains a negative impression of the sole of the foot which is corrected by the presence of the said first negative impression.

Another advantage of the invention is to make local relief corrections to the negative impressions by raising the said enclosures and by locally pressing on the lower flexible wall of the said lower enclosure or the said second enclosure whilst the latter is connected to the said vacuum device.

One device according to the invention is of the type comprising at least one sealed enclosure having at least one flexible wall which is filled with a granular material and which may be connected to a suction device by means of a valve.

One device according to the invention is characterized by the fact that it includes at least two horizontal rigid superimposed frames, each being equipped with a flexible upper wall and a flexible lower wall which, with the said frame, delimit a sealed enclosure which is connected to a suction device by means of a flexible duct fitted with a valve and which is filled with a granular material.

According to one preferred mode of embodiment, one device according to the invention comprises a third rigid moveable frame which may be superimposed onto the second frame, which is equipped with a flexible upper wall and a flexible lower wall, which, along with the said third frame, delimit a sealed enclosure which is filled with a granular material and which is connected to a suction device by means of a flexible duct fitted with a valve.

The invention provides devices which enable a negative impression of the foot to be obtained, of correcting this impression, and of then obtaining an additional positive impression of the corrected negative impression, of locally correcting the positive impression and of obtaining a new additional negative impression of the corrected positive impression so as to produce corrective soles which do not merely reproduce the shape of the foot, but which tend to correct the posture of the foot.

The devices of the invention enable many corrections to be made.

Initially, they allow a negative impression to be taken of a foot placed in a given position by inserting corrective elements under the lower wall of the lower enclosure which is flexible so that these corrective elements may exert an effect on the posture of the foot.

They also enable local corrections to be made to a negative impression and not merely recessed corrections obtained by pressing locally on the upper face which retains the said negative impression in order to drive back the granular material, but also relief corrections of the upper face. These relief corrections are obtained by raising the enclosures in order to gain access to the flexible lower faces and by pressing locally on the latter so as to move the granular materials towards the upper face.

The devices according to the invention allow for softening of the curve of the local corrections of a first negative impression by obtaining a second negative impression of the first negative impression once the latter has been corrected.

The devices according to the invention also enable an additional positive impression of a corrected negative impression to be obtained, which allows for local recessed corrections to be made to the positive impression and then to reproduce these corrections in relief on an additional negative impression of the corrected positive impression.

All these corrections can be obtained by intervening on the flexible walls of the enclosures whilst the latter are in contact with the suction device, which facilitates the movements of the granular materials and avoids the formation of folds or bubbles.

The methods of devices according to the invention make it possible to simply, quickly and cheaply obtain many ways to correct the initial impression to finally produce a sole or corrective shoe.

They allow for obtaining better control of the width of the impressions with a view to obtaining better adaptation of the corrective sole as regards a defined type of shoe.

They enable enveloping impressions to be obtained which comes up to the sides of the foot, which allows for orthetic devices to be embodied which are more effective by improving supporting the foot at the side and rear.

BRIEF DESCRIPTION OF THE DRAWINGS

The following description refers to the annexed drawings which, in no way restrictive, represent an example of embodiment of a device as claimed in the invention and the stages of the various methods as claimed in the invention.

DETAILED DESCRIPTION OF THE PREFERRED EMBODIMENTS

Figure 1:
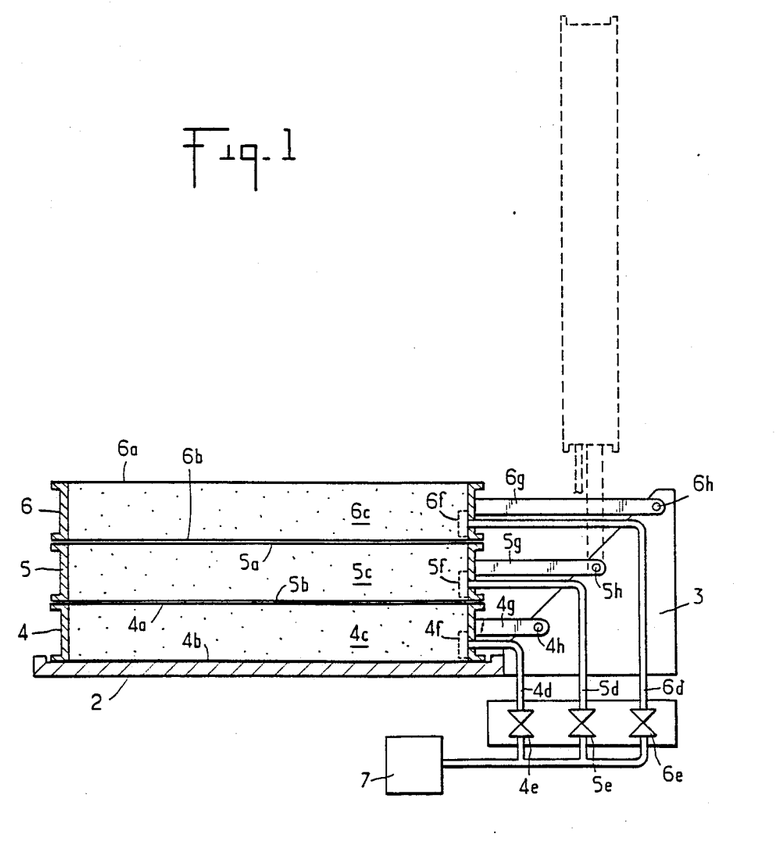
FIG. 1 is a vertical section of a preferred mode of embodiment of a device as claimed in the invention.

FIG. 1 shows a device which comprises a fixed frame consisting preferably of a flat seat 2 placed on a flat horizontal surface and two vertical stanchions 3.

It includes three identical superimposed rectangular frames 4, 5 and 6 composed, for example, of U-shaped sections.

These rigid frames are longer than the length of the largest feet and are wider than the normal width of one foot or two feet, so that one foot or two feet can be placed inside the said frames. Each frame carries two flexible ductile walls, an upper wall 4a, 5a, 6a and a lower wall 4b, 5b, 6b which are made up, for example, of sheets made of a flexible plastic material stretched across the frame.

These walls are assembled sealed with the corresponding frame so that each frame and the two flexible walls which equip it delimit an enclosure 4c, 5c, 6c which is filled with a granular material, for example glass microballs or a plastic material with a diameter of about one millimeter.

In one variant, the two flexible walls equipping each frame may be replaced by a ductile pocket, for example a plastic bag secured to the perimeter of the frame, preferably in such a way that the upper wall is taut.

The height of the frames 4, 5 and 6 is about 2 to 12 centimeters.

Each enclosure 4c, 5c, 6c is connected by a small flexible duct 4d, 5d, 6d to a suction device 7 which, for example, is a vacuum pump passing through a valve 4e, 5e, 6e, which enables the enclosure to be separated from the device 7. The device 7 sucks the air contained in the enclosure so that it creates a vacuum inside the latter which enables the particles it contains to be solidified in a given configuration, which enables an impression to be retained in a known form.

The extremity of each duct 4d, 5d, 6d, which respectively opens into the enclosures 4c, 5c, 6c, is equipped with a filter 4f, 5f, 6f which stops the pump 7 sucking up the particles contained in the enclosure.

Provision of the seat 2 is not obligatory. In one variant, the lower frame 4 can be laid directly on a horizontal floor.

FIG. 1 shows a mode of embodiment wherein each frame 4, 5 and 6 is connected by one or more arms 4g, 5g, 6g to a horizontal hinge pin 4h, 5h, 6h borne by the two stanchions 3 so that it is possible to lift each frame up to vertical in order to gain access to the lower flexible wall whilst the corresponding enclosure is in communication with the suction device 7.

By way of illustration, the raised position of frame 5 has been shown by dots on FIG. 1. The hinge pins 4h, 5h, 6h are disposed inside a transversal plane inclined at 45° to horizontal to enable the frames 4, 5 and 6 to be raised side by side.

Because the frames are connected by arms to the joints secured to the supporting structure, these are automatically superimposed when they are folded down to horizontal.

Of course, it is possible to arrive at the same result by other mechanical means, for example by having the frames 4, 5 and 6 slide onto guiding rods or between vertical slide rails.

FIG. 1 shows a preferred example wherein the three frames 4, 5 and 6 are identical and can be superimposed.

According to one variant, the upper frame 6 can be smaller and cannot be connected to the fixed supporting structure.

Figure 2:
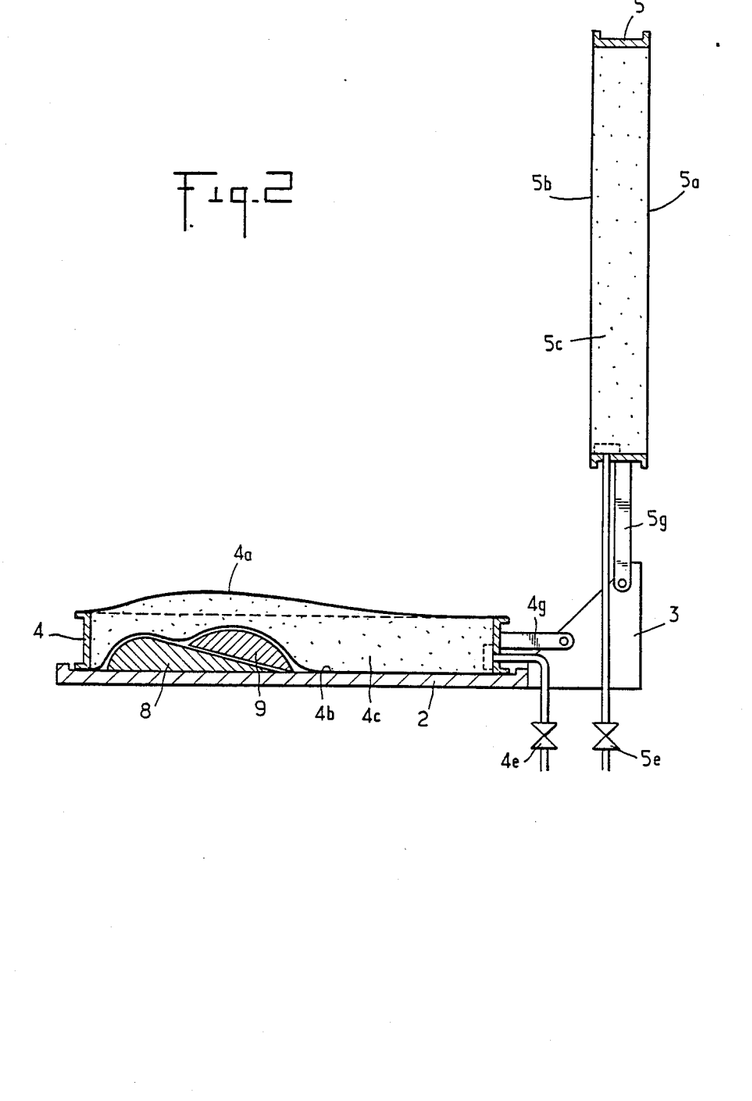
FIGS. 2 to 7 show in vertical sections the 0 successive stages of the methods as claimed in the invention using a device as claimed in figure 1.

FIG. 2 shows in a vertical section a first stage of a method as claimed in the invention using a device according to FIG. 1 which only comprises two frames 4 and 5 connected to a supporting structure 2, 3.

In this first stage, the frame 5 is raised up. Under the lower wall 4b of the enclosure 4c, correction elements are placed designed to force the foot to take up a specific posture when one takes up the negative impression of the sole of the foot.

These corrective elements comprise, for example, a heel piece 8 which is to be found under the heel in order to force the foot to be inclined towards the front in a position similar to that it occupies in a shoe provided with relatively high heels. Another corrective element, which may be used solely or in combination with a heel piece, is a plantar arch corrector 9 which forces the foot to take up an arched position. Under the lower wall 4b, it is thus possible to place adjusting templates or other precorrective elements.

Figure 3:
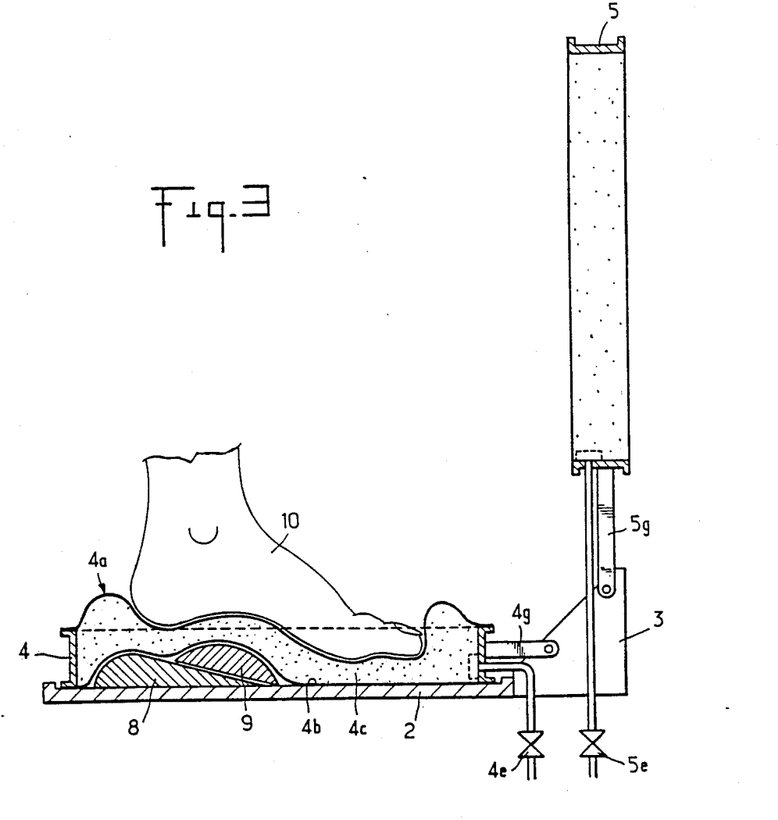

FIG. 3 is a vertical section similar to FIG. 2, which shows the next stage of the method wherein the foot 10 of the patient rests on the upper wall 4a so that the granular material contained in the enclosure 4c moves and the enclosure 4c is placed in a vacuum by opening the valve 4e which puts it in communication with the suction device 7, which solidifies the solid particles so that the wall 4a is set in a shape which constitutes a negative impression of the sole of the foot 10.

The term "negative impression" is used to denote an additional impression wherein the hollows of the foot are replaced by relief bosses and the reliefs by recessed parts. The term "positive impression" is used to denote an impression which directly reproduces the shape of the foot.

The negative impression obtained does not reproduce merely the shape of the foot laid flat. It is an impression which is corrected by the fact that corrective elements are placed under the flexible wall 4b and, because of the deformability of the latter and the slight thickness of the enclosure 4c, these corrective elements have forced the foot to assume a specific position during taking of the impression.

FIGS. 2 and 3 thus show a first possibility offered by the devices as claimed in the invention in order to correct the negative impression of a foot so as to then obtain a corrective sole. It will be observed that this first negative impression correction is effected whilst sucking occurs into the cavity 4c by means of the device 7, the aim of this being to facilitate the influence the corrective elements 8, 9 placed under the wall 4b exert on the position of the foot.

When the foot 10 is pressed onto the flexible wall 4a, the particles situated under the foot tend to migrate externally outside the zone subjected to the pressure of the foot so that at the end of the stage represented on FIG. 3, the thickness of the enclosure 4c is slightly under the foot and the wall 4a moves forward, backwards and onto the sides of the foot and a negative impression is obtained which includes the raised edges which slightly envelop the corrected impression of the sole of the foot. The fact that the thickness of the enclosure 4c is extremely slight under the sole of the foot ensures that it roughly matches the contour of the corrective elements 8 and 9. This result could not be attained with an enclosure 4c whose lower wall 4b would not be flexible.

Once the corrected negative impression of the lower face of the foot has been taken, it is still possible to make corrections to this impression by locally pressing on the wall 4a to locally drive back the granular material so as to make recessed corrections.

By means of one device as claimed in the invention, it is also possible to make localized relief corrections to the negative impression.

In order to do this, after having removed the foot 10, the frame 4 is lifted up, which allows to gain access to the lower flexible wall 4b and it is then possible to locally push back this wall, either manually or by means of a tool in order to move the granular material contained in the enclosure 4c so that it locally drives back the upper wall 4a outwards, thus correcting the shape of the latter.

These localized recessed or relief corrections of the negative impression are carried out whilst the enclosure 4c is connected to the device 7, namely whilst the valve 4e is open, so that suction facilitates the movement of the solid particles inside the enclosure and enables localized corrections to be made without any risk of folds being formed on the wall 4a or air bubbles in the enclosure 4c.

Localized recessed or relief modelling of the wall 4a constitutes a second possibility offered by the devices as claimed in the invention so as to make corrections to the negative impression of the sole of a foot in order to subsequently obtain a corrective sole.

Figure 4:
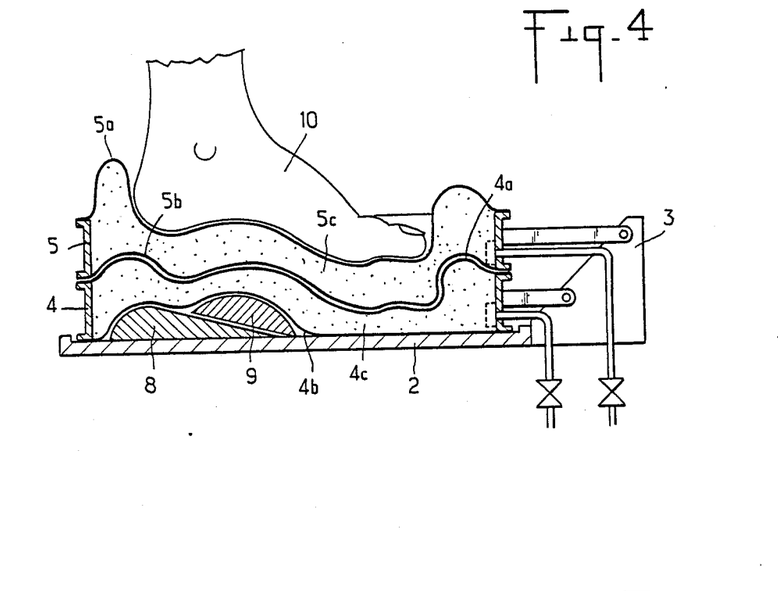

In a vertical section, FIG. 4 shows a next stage of the method as claimed in the invention.

This figure shows the two frames 4 and 5 superimposed.

The enclosure 4c is in a vacuum and the upper wall 4a forms a first corrected negative impression of the sole of the foot 10.

After having lowered the frame 5, which brings the enclosure 5c above the negative impression 4a, the foot 10 is pressed again onto the upper wall 5a of the second enclosure whilst the latter is placed in communication with the suction device 7 so that a second negative impression formed by the wall 5a is obtained.

During this operation, the first negative impression 4a, which has already been corrected, adopts the role played by the elements 8 and 9 during assuming the first impression.

It leans against and deforms the flexible wall 5b, the aim of this being to drive back the granular materials and force the foot 10 to take up a position corrected in relation to its natural position.

The corrections made to the first impression 4a have repercussions on the second negative impression 5a, but in an attenuated form, which enables the shapes and slopes of the corrections to be softened, which previously would be too emphasized. Moreover, the granular materials contained in the enclosure 5c are pushed back onto the sides of the foot and which are already occupied by the raised edges of the first impression 4a so that it is thus possible to obtain a second negative impression 5a which is again corrected in relation to the first one and which is more envelopping, namely that its edges are lifted higher at the front, rear and on the sides of the sole of the foot without losing any precision of the corrected negative impression.

If required, it is possible, either manually or by means of a tool, to obviously make local recessed or relief retouches to this second negative impression 5a, in the same way as those made for the first one, whilst the enclosure 5c is connected to the suction device.

During the operation represented on FIG. 4, the lower wall 5b of the second enclosure 5c takes the exact shape of the wall 4a and after the enclosure 5c has been placed in a vacuum, it retains its shape which constitutes a positive impression of the corrected negative impression 4a.

It is also possible to use this positive impression to shape a corrective sole, for example by placing between the walls 4a and 5b a hot thermoformable plate which takes the exact corrected shape and which constitutes a corrective sole.

It is also possible to have the enclosure returned so as to place the positive impression 5b on the top and to have slide into the latter a hardenable material, such as a polymerizable resin which on hardening is transformed into a thick corrective sole whose face placed in contact with the wall 5b shall constitute the upper corrective face which will be placed in contact with the sole of the foot.

So as to make the most of the possibilities of corrections offered by the second negative impression 5a, a second positive impression is preferably used which reproduces the form of the second corrected negative impression 5a.

Figure 5:
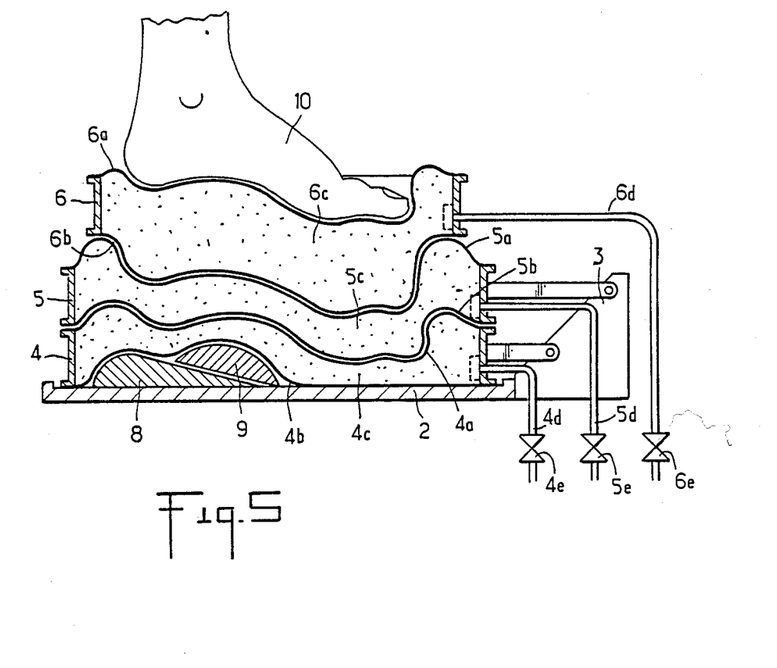

FIG. 5 shows a next stage of a method as claimed in the invention in which an additional positive impression of the second negative impression 5a is obtained.

FIG. 5 shows the lower frame 4 equipped with two flexible walls 4a, 4b, the upper wall 4a retaining a first corrected negative impression, and a second frame 5 equipped with two flexible walls 5a, 5b, the upper wall 5a reproducing a second corrected negative impression of the sole of the foot.

A third rigid frame 6 is used equipped with two flexible walls 6a, 6b which delimit an enclosure 6c filled with a divided material which can be placed in communication with a suction device via a flexible duct 6d.

FIG. 5 shows an example in which the frame 6 is smaller than the frames 4 and 5 and is not joined to the fixed supporting structure 3. In one variant, the frame 6 may be identical to the frames 4 and 5 and joined to the supporting structure 3, as shown in FIG. 1.

Once the frame 6 is put in place, the patient is asked to press his foot 10 onto the upper wall 6a so that the lower wall 6b takes the exact shape of the wall 5a it touches and the valve 6e opens which puts the enclosure 6c in communication with the suction device 7.

During this stage, the pressure of the foot 10 can be replaced by that of a standard foot shape.

Once the positive impression of the foot has been assumed, it is possible to locally recessed correct this. In order to do that, the foot is removed and the frame 6 is lifted up in order to gain access to the wall 6b whilst leaving the valve 6e open, and the wall 6b is locally pressed in order to drive back the materials contained in the enclosure 6c.

This possibility of locally making recessed corrections to the positive impression formed by the wall 6b enables relief corrections of the negative impression 5a to be obtained.

Once the positive impression 6b is corrected, the frame 6 is put back onto the frame 5 and the enclosure 5c is placed in communication with the device 7 so that the upper wall 5a gets out of shape and takes the exact form of the wall 6b, namely a shape which constitutes a negative impression to which local relief corrections have been made which reproduce the recessed corrections made to the wall 6b.

Figure 6:
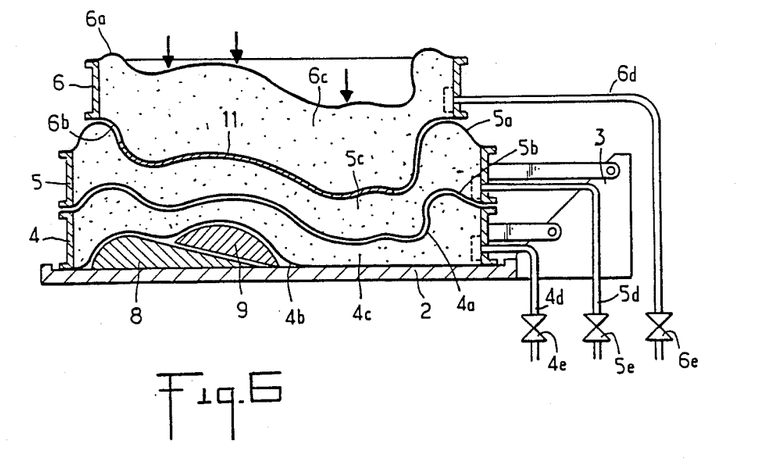

It is then possible to use the corrected negative impression 5a and the positive impression 6b which are complementary in order to produce a corrective orthopedic sole, as shown on FIG. 6.

During this stage, a thermoplastic sheet 11 is placed between the wall 5a and the wall 6b, the enclosures 5c and 6c being in a partial vacuum so that they are dimensionally stable, and pressure is exerted on the wall 6a so that, after hardening the sheet 11 constitutes a corrective sole which can be placed inside a shoe.

FIG. 6 shows that this corrective sole can rise to the rear of the heel. It can also rise onto the lateral sides of the foot so that it more effectively holds up the foot in the sought-after corrective position.

Figure 7:
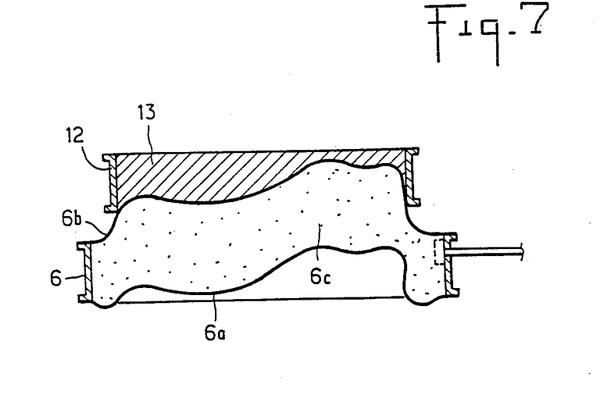

FIG. 7 represents a use variant of the corrected positive impression 6b.

According to this variant, the frame 6 is returned so that the wall 6b, which constitutes the corrected positive impression, is above.

Placed around the central part of the positive enclosure 6b is a sealed formwork 12 whose bottom is constituted by the wall 6b and into the bottom a hardenable liquid material is poured, for example latex or a polymerizable resin. After hardening, a thick corrective sole 13 is obtained with an upper face roughly horizontal, and a lower face which takes the exact contour of the wall 6b. This sole is returned and placed inside a shoe.

One device as claimed in the invention makes it possible to produce soles, known as proprioceptive soles, which comprise relief elements placed at properly determined locations in order to excite certain muscles and thus provoke automatic correction of the position of the foot.

In order to obtain soles comprising these corrective relief elements, it merely requires that in the negative impression 4a or 5a well-localized recessed corrections be made, which shall result in relief elements occurring on the corrective sole.

One device as claimed in the invention also enables soles or sole elements to be reproduced or to embody assemblies of several sole elements by using two superimposed enclosures.

A flat plate is placed between the two enclosures and one of these two enclosures is placed in a vacuum, for example namely the lower enclosure when they are drawn nearer to each other.

The upper enclosure is lifted up, the plate is removed, the elements to be reproduced are recessed printed onto the upper wall of the lower enclosure and then a hardenable liquid is poured onto the lower wall which creates a proprioceptive or corrective sole.

It is also possible to take an additional positive impression by pressing the second enclosure when placed in a vacuum, then a thermoformable plate is placed between the two enclosures and the two enclosures draw together in order to obtain a proprioceptive or receiving sole.

What is claimed is:

1. A method to obtain a corrected negative impression of the foot so as to produce a corrective sole comprising the following steps:
   filling a first sealed enclosure comprising a rigid frame, an upper flexible wall and a lower flexible wall with granular materials;
   connecting said sealed enclosure to a suction device;
   pressing the bottom of the foot on said upper flexible wall;
   sucking air contained in said enclosure with said suction device in order to create a vacuum inside said enclosure which stiffens said granular materials so that said upper flexible wall forms a negative impression of the bottom of the foot;
   and pressing locally on the lower flexible wall of said enclosure whilst said suction device is sucking air from said enclosure in order to make relief corrections to said negative impression formed in said upper flexible wall.

2. A method to obtain a corrected impression of a foot so as to produce a corrective sole comprising the following steps:
   filling a first sealed enclosure comprising a rigid frame, an upper flexible wall and a lower flexible wall with granular materials;
   connecting said sealed enclosure to a suction device;
   pressing the bottom of the foot on said upper flexible wall;
   sucking air contained in said enclosure with said suction device in order to create a vacuum inside said enclosure which stiffens said granular materials so that said upper flexible wall forms a negative impression of the bottom of the foot;
   correcting said negative impression whilst said enclosure is connected to said suction device which sucks air from said enclosure;
   placing a second sealed enclosure comprising a rigid frame, an upper flexible wall and a lower flexible wall on said first sealed enclosure, which second enclosure is filled with granular materials and connected to said suction device;
   pressing said foot on the upper wall of said second enclosure;
   sucking air from said second enclosure so that said lower wall of said second enclosure conforms to the shape of the upper wall of said first enclosure to form a positive impression of said foot;
   raising said second enclosure and recessing locally said lower wall of said second enclosure whilst said suction device is sucking air from said enclosure in order to correct locally said positive impression;
   placing again said second enclosure onto said first enclosure and pressing said corrected positive impression against the upper wall of said first enclosure whilst said suction device is sucking air from said first enclosure in order to correct the negative impression on the first enclosure upper walls;
   and making a corrective sole using said corrected positive impression.

3. A method according to claim 2 comprising making a corrective sole using said corrected positive impression in connection with said corrected negative impression.

* * * * *